United States Patent
Isozaki et al.

(10) Patent No.: US 10,333,491 B2
(45) Date of Patent: Jun. 25, 2019

(54) OSCILLATOR, ELECTRONIC APPARATUS, AND MOVING OBJECT

(71) Applicant: Seiko Epson Corporation, Tokyo (JP)

(72) Inventors: Shigenori Isozaki, Tatsuno (JP); Akihiro Fukuzawa, Hino (JP); Toshimasa Usui, Chino (JP)

(73) Assignee: Seiko Epson Corporation (JP)

( * ) Notice: Subject to any disclaimer, the term of this patent is extended or adjusted under 35 U.S.C. 154(b) by 131 days.

(21) Appl. No.: 15/344,814

(22) Filed: Nov. 7, 2016

(65) Prior Publication Data

US 2017/0134004 A1 May 11, 2017

(30) Foreign Application Priority Data

Nov. 10, 2015 (JP) ................... 2015-220119

(51) Int. Cl.

| | |
|---|---|
| *G02F 1/39* | (2006.01) |
| *H01Q 1/38* | (2006.01) |
| *H03B 5/18* | (2006.01) |
| *H03B 5/36* | (2006.01) |
| *H03B 7/08* | (2006.01) |
| *H03B 7/14* | (2006.01) |
| *H03H 9/05* | (2006.01) |
| *H03H 9/19* | (2006.01) |
| *H03K 3/13* | (2006.01) |
| *H01Q 11/08* | (2006.01) |
| *G01N 21/3581* | (2014.01) |

(52) U.S. Cl.
CPC .......... *H03H 9/19* (2013.01); *G01N 21/3581* (2013.01); *H01Q 1/38* (2013.01); *H01Q 11/08* (2013.01); *H03B 5/18* (2013.01); *H03B 5/362* (2013.01); *H03B 5/368* (2013.01); *H03B 7/08* (2013.01); *H03B 7/14* (2013.01); *H03H 9/0542* (2013.01); *H03K 3/13* (2013.01); *G02F 1/39* (2013.01)

(58) Field of Classification Search
CPC .......... H03L 7/00; H03H 9/19; H03H 9/0542; H03B 5/362; H03B 5/368; H03B 5/18; H03B 7/08; H03B 7/14; G01N 21/3581; G02F 1/39; H01Q 11/08; H03K 3/13
USPC .................. 331/108 C, 116 FE, 117 FE, 158
See application file for complete search history.

(56) References Cited

U.S. PATENT DOCUMENTS

| | | | |
|---|---|---|---|
| 6,661,295 B2 * | 12/2003 | Knecht | .................. H03L 1/025 331/158 |
| 8,736,390 B2 | 5/2014 | Ozawa et al. | |
| 2016/0226447 A1 | 8/2016 | Fukuzawa | |

FOREIGN PATENT DOCUMENTS

| | | |
|---|---|---|
| JP | 2006-054269 A | 2/2006 |
| JP | 2012-186784 A | 9/2012 |
| JP | 2016-144128 A | 8/2016 |

* cited by examiner

*Primary Examiner* — Arnold M Kinkead
(74) *Attorney, Agent, or Firm* — Harness, Dickey & Pierce, P.L.C

(57) ABSTRACT

An oscillator includes a package having a first side, a second side, a third side, and a fourth side, a resonator and an oscillation circuit disposed in the package, an output terminal arranged along the first side of the package, and outputting a clock signal generated by the oscillation circuit, and a control terminal arranged along the second side of the package, and supplied with a digital control signal adapted to update an operation state of the oscillation circuit.

7 Claims, 6 Drawing Sheets

701

OSCILLATOR, ELECTRONIC APPARATUS, AND MOVING OBJECT

BACKGROUND

1. Technical Field

The invention relates to an oscillator configured by mounting a resonator and an oscillation circuit in a package. Further, the invention relates to an electronic apparatus, a moving object, and so on using such an oscillator.

2. Related Art

In some cases, for example, a quartz crystal oscillator is configured by mounting a quartz crystal resonator and a semiconductor device (IC) in a package. In such a quartz crystal oscillator, in some cases, the characteristic of the quartz crystal resonator is improved by overdriving the quartz crystal resonator, or the quartz crystal resonator is connected to an external measurement device to check the characteristic prior to mounting the IC using two monitor terminals connected to the quartz crystal resonator. Therefore, in general, the wiring pattern for connecting the quartz crystal resonator and the monitor terminals is elongated, and becomes easy to be affected by an external noise such as a noise from a digital circuit. As a result, there is a problem that the oscillation frequency is shifted from a preset value, or a phase distortion is generated.

As a related-art technology, in JP-A-2012-186784 (paragraphs 0021-0022, FIG. 1) (Document 1), there is disclosed a quartz crystal oscillation device having a semiconductor package and a quartz crystal resonator mounted on a wiring board. The semiconductor package is provided with a first external terminal and a second external terminal used for connecting the quartz crystal resonator. On the wiring board, there are formed a first wiring pattern extending from the first external terminal and connected to one end of the quartz crystal resonator, and a second wiring pattern extending from the second external terminal in roughly the same direction as the first wiring pattern and connected to the other end of the quartz crystal resonator.

Further, on the wiring board, there is formed a third wiring pattern disposed in an area between the first wiring pattern and the second wiring pattern, and electrically connected to a ground power supply voltage. Thus, it becomes possible to reduce the pin-to-pin parasitic capacitance between the first external terminal and the second external terminal, and to reduce the pin-to-pin coupling noise. As a result, it is possible to satisfy the requirement of reduction of the parasitic capacitance and improvement of noise immunity.

Further, JP-A-2006-54269 (paragraphs 0001-0005, FIG. 1) (Document 2) discloses a piezoelectric oscillator configured by combining an IC having the oscillation circuit, the temperature compensation circuit, the memory circuit, and so on integrated with each other and a piezoelectric resonator with each other. This piezoelectric oscillator is characterized in that a first analog circuit block including a temperature compensation circuit, a second analog circuit block including an oscillation circuit, and a digital circuit block including a memory circuit are integrated into a piezoelectric oscillator IC, and in the piezoelectric oscillator IC, the first analog circuit block and the second analog circuit block are disposed separately from each other, and the digital circuit block is disposed so as to intervene between these analog circuit blocks.

In this piezoelectric oscillator, the digital circuit is used only for writing data to the memory in an adjustment operation in the factory when producing a TCXO, and there is no chance to operate the digital circuit in the state in which the piezoelectric oscillator is used as the TCXO. Therefore, the object is to prevent the malfunction of the piezoelectric oscillator caused by interference between an AC circuit block and a DC circuit block in the analog circuit. An example of the interference is as follows. An AC operation of the oscillation circuit causes a noise in the DC circuit, and thus, the phase noise, which is an important characteristic of the quartz crystal oscillator, is affected.

Document 1 discloses the improvement of the noise immunity of the first external terminal and the second external terminal to be connected to the quartz crystal resonator, but does not particularly disclose the improvement of the noise immunity of other terminals. Further, unlike the piezoelectric oscillator disclosed in Document 2, in such an oscillator as a digitally controlled crystal oscillator (DCXO) in which the oscillation frequency is dynamically digitally controlled during an oscillation operation, a digital control signal interferes an analog oscillation signal to affect the phase noise characteristic, and thus, the oscillation accuracy is deteriorated.

SUMMARY

A first advantage of some aspects of the invention is to reduce the deterioration of the oscillation accuracy due to the interference by the digital control signal or the like in the oscillator the oscillation frequency of which is dynamically digitally controlled during the oscillation operation. A second advantage of some aspects of the invention is to provide an electronic apparatus and a moving object using such an oscillator.

An oscillator according to a first aspect of the invention includes a package having a first side, a second side, a third side, and a fourth side, a resonator and an oscillation circuit disposed in the package, an output terminal arranged along the first side of the package, and outputting a clock signal generated by the oscillation circuit, and a control terminal arranged along the second side of the package, and supplied with a digital control signal adapted to update an operation state of the oscillation circuit.

According to the first aspect of the invention, by disposing the output terminal for outputting the clock signal and the control terminal to be supplied with the digital control signal respectively on the different sides of the package in the oscillator the oscillation frequency of which is dynamically digitally controlled during the oscillation operation, it is possible to increase the distance between the wiring pattern for transmitting the clock signal and the wiring pattern for transmitting the digital control signal to thereby reduce the capacitive coupling between the wiring pattern for transmitting the clock signal and the wiring pattern for transmitting the digital control signal, and thus reduce the deterioration of the oscillation accuracy due to the interference by the digital control signal.

The oscillator may further include a first wiring pattern and a second wiring pattern disposed in the package, electrically connecting a pair of terminals of the resonator and the oscillation circuit to each other, and extending toward the third side of the package. With this configuration, it is possible to make the first and second wiring patterns sensitive to the noise distant from the transmission paths of the clock signal and the digital control signal to reduce the capacitive coupling between the wiring patterns and the transmission paths of the clock signal and the digital control signal, and thus reduce the deterioration of the oscillation accuracy due to the interference by the clock signal and the digital control signal.

The oscillator may further include a third wiring pattern disposed in the package, electrically connected to the output terminal, and having no crossing with the first and second wiring patterns in a planar view, and a fourth wiring pattern disposed in the package, electrically connected to the control terminal, and having no crossing with the first through third wiring patterns in the planar view. With this configuration, it is possible to reduce the coupling capacitance between the first and second wiring patterns sensitive to the noise, the third wiring pattern for transmitting the clock signal, and the fourth wiring pattern for transmitting the digital control signal to thereby reduce the deterioration of the oscillation accuracy due to the interference by the clock signal and the digital control signal.

The oscillator may further include a fifth wiring pattern disposed between one of the first and second wiring patterns and one of the third and fourth wiring patterns in the package, and electrically connected to a power supply terminal supplied with one of a power supply potential and a reference potential. With this configuration, it is possible to further reduce the coupling capacitance between the first or second wiring pattern sensitive to the noise and the third or fourth wiring pattern for transmitting the clock signal or the digital control signal to thereby further reduce the deterioration of the oscillation accuracy due to the interference by the clock signal or the digital control signal.

In the aspect of the invention, at least one semiconductor device constituting the oscillation circuit may have a first terminal arranged along a side, which is closest to the first side of the package, of the semiconductor device, and adapted to output the clock signal, and a second terminal arranged along a side, which is closest to the second side of the package, of the semiconductor device, and supplied with the digital control signal. With this configuration, it is possible to shorten the wiring pattern for connecting the first terminal of the semiconductor device and the output terminal to each other, and shorten the wiring pattern for connecting the second terminal of the semiconductor device and the control terminal to each other to thereby reduce the capacitive coupling between the wiring pattern for connecting the first terminal of the semiconductor device and the output terminal to each other and the wiring pattern for connecting the second terminal of the semiconductor device and the control terminal to each other, and thus reduce the deterioration of the oscillation accuracy due to the interference by the digital control signal.

An oscillator according to a second aspect of the invention includes a package, a resonator and an oscillation circuit disposed in the package, a first wiring pattern and a second wiring pattern disposed in the package, and adapted to electrically connect a pair of terminals of the resonator and the oscillation circuit to each other, a third wiring pattern disposed in the package, electrically connected to an output terminal adapted to output a clock signal generated by the oscillation circuit, and having no crossing with the first and second wiring patterns in a planar view, a fourth wiring pattern disposed in the package, electrically connected to a control terminal supplied with a digital control signal adapted to update an operation state of the oscillation circuit, and having no crossing with the first through third wiring patterns in the planar view, and a fifth wiring pattern disposed between one of the first and second wiring patterns and one of the third and fourth wiring patterns in the package, and electrically connected to a power supply terminal supplied with one of a power supply potential and a reference potential.

According to the second aspect of the invention, in the oscillator the oscillation frequency of which is dynamically digitally controlled during the oscillation operation, it is possible to reduce the coupling capacitance between the first and second wiring patterns sensitive to the noise, the third wiring pattern for transmitting the clock signal, and the fourth wiring pattern for transmitting the digital control signal to thereby reduce the deterioration of the oscillation accuracy due to the interference by the clock signal and the digital control signal.

An electronic apparatus according to a third aspect of the invention includes any one of the oscillators described above. A moving object according to a fourth aspect of the invention includes any one of the oscillators described above. According to the third or the fourth aspect of the invention, it is possible to provide an electronic apparatus or a moving object operating with the accurate clock signal generated using the oscillator in which the deterioration of the oscillation accuracy due to the interference by the digital control signal and so on is reduced.

BRIEF DESCRIPTION OF THE DRAWINGS

The invention will now be described with reference to the accompanying drawings, wherein like numbers reference like elements.

DESCRIPTION OF EXEMPLARY EMBODIMENTS

Some embodiments of the invention will hereinafter be explained in detail with reference to the drawings. It should be noted that the same constituents are denoted by the same reference symbols, and the duplicated explanation will be omitted. In the following embodiments, as an example of the oscillator, there is described a quartz crystal oscillator using a quartz crystal resonator.

First Embodiment

Figure 1:
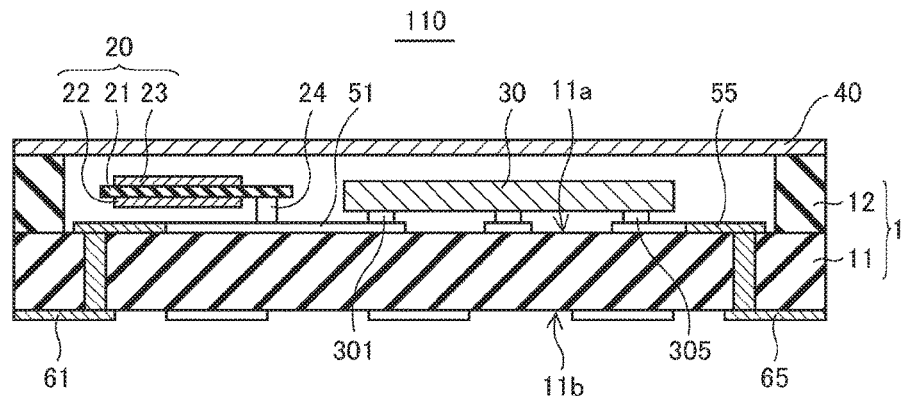
FIG. 1 is a cross-sectional view of a quartz crystal oscillator according to a first embodiment of the invention.

FIG. 1 is a cross-sectional view of the quartz crystal oscillator according to the first embodiment of the invention. As shown in FIG. 1, the quartz crystal oscillator 110 includes a package 10, a quartz crystal resonator 20 and a semiconductor device (IC) 30 mounted in a cavity provided to a principal surface (the upper surface in the drawing) of the package 10, and a lid part 40 for covering the quartz crystal resonator 20 and the semiconductor 30.

The package 10 is configured by, for example, stacking a second substrate 12 constituting a sidewall on a first substrate 11. The first substrate 11 and the second substrate 12 are each formed of an insulating material such as ceramic. The first substrate 11 has a first surface 11a and a second surface 11b opposed to each other. The first surface 11a and the second surface 11b can also be roughly parallel to each other.

The second substrate 12 forms a sidewall projected from the first surface 11a of the first substrate 11 in the peripheral area of the first surface 11a. The first substrate 11 and the sidewall constitute a package 10 having a cavity for housing the quartz crystal resonator 20 and the semiconductor device 30. The package 10 is capable of safely protecting the quartz crystal resonator 20 and the semiconductor device 30.

The quartz crystal resonator 20 is disposed on the first surface 11a of the first substrate 11 in the package 10, and has a quartz crystal element 21, which is a piezoelectric material, as a resonator element, a first electrode 22 and a second electrode 23 sandwiching the quartz crystal element 21, and a pair of terminals 24 for electrically connecting these electrodes 22, 23 to a wiring layer provided to the first surface 11a. By applying an alternating-current voltage between the electrode 22 and the electrode 23 via the pair of terminals 24, a mechanical vibration of the quartz crystal resonator 20 is excited due to the piezoelectric effect.

Further, the lid part 40 for covering the quartz crystal resonator 20 and the semiconductor device 30 is bonded to the sidewall (the second substrate 12) disposed in the peripheral area of the first surface 11a of the first substrate 11. The lid part 40 is formed of, for example, iron (Fe), cobalt (Co), nickel (Ni), an alloy of any of these materials, or the like. In the cavity in which the quartz crystal resonator 20 and the semiconductor device 30 are housed, there can also be encapsulated an inert gas such as helium.

The semiconductor device 30 is disposed on the first surface 11a of the first substrate 11 in the package 10, and is electrically connected to the electrodes 22 and 23 of the quartz crystal resonator 20 via the wiring layer disposed on the first surface 11a and the pair of terminals 24 of the quartz crystal resonator 20. The semiconductor device 30 incorporates an oscillation circuit, and performs the oscillation operation at an oscillation frequency controlled by digital control signals to thereby generate a clock signal. The semiconductor device 30 can also be, for example, a semiconductor chip (a bare chip) not encapsulated in a package. The bare chip is mounted on the first surface 11a of the first substrate 11 using flip-chip bonding or the like.

Figure 2:
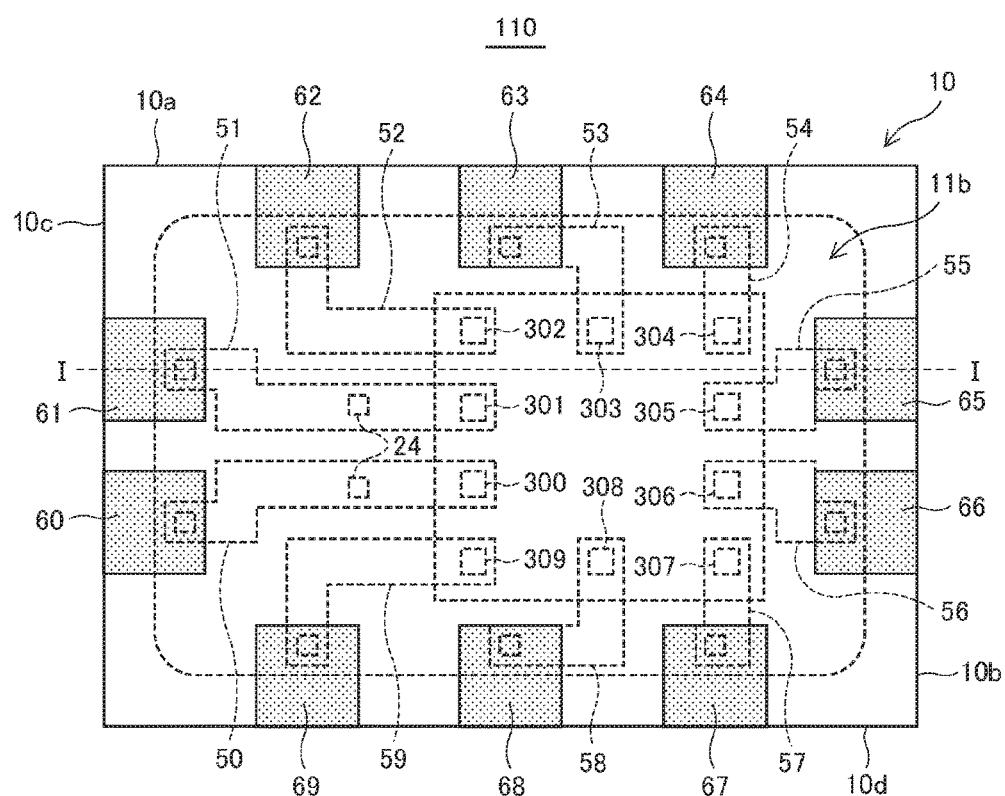
FIG. 2 is a bottom view of the quartz crystal oscillator shown in FIG. 1.

FIG. 2 is a bottom view of the quartz crystal oscillator shown in FIG. 1. The line I-I in FIG. 2 indicates the position of the cross-section shown in FIG. 1. As shown in FIG. 2, the package 10 has four sides 10a through 10d. In the example shown in FIG. 2, the side 10a and the side 10d are roughly parallel to each other, the side 10b and the side 10c are roughly parallel to each other, and the side 10a and the side 10b are roughly perpendicular to each other.

The quartz crystal oscillator 110 has a wiring layer including a plurality of wiring patterns 50 through 59 disposed on the first surface 11a of the first substrate 11 in the package 10. A part of each of the wiring patterns constitutes an IC connection pad to be electrically connected to one of the terminals of the semiconductor device 30.

Further, The quartz crystal oscillator 110 has a plurality of external connection terminals 60 through 69 disposed on the second surface 11b of the first substrate 11 in the package 10. The first substrate 11 is provided with a plurality of through holes, and the wiring patterns 50 through 59 and the external connection terminals 60 through 69 are electrically connected respectively to each other via these through holes.

The wiring patterns 50 through 59, and the external connection terminals 60 through 69 are each formed of an electrically-conductive material such as aluminum (Al) or copper (Cu). Further, the plurality of through holes is filled with an electrically-conductive material such as aluminum (Al), copper (Cu), or tungsten (W).

The external terminals 60, 61 are used as monitor terminals electrically connected respectively to the electrodes 22, 23 via the pair of terminals 24 of the quartz crystal resonator 20. Before mounting the semiconductor device 30, by trimming the electrode 23 with a laser or the like while making probe needles have contact with the monitor terminals 60, 61 to measure the resonance characteristic of the quartz crystal resonator 20 using an external device, the resonance frequency of the quartz crystal resonator 20 is adjusted.

Alternatively, there is performed a process of overdriving the quartz crystal resonator 20 to improve the characteristic by making the probe needles have contact with the monitor terminals 60, 61 to apply a high alternating-current voltage to the electrodes 22, 23 of the quartz crystal resonator 20. Further, it is also possible to connect the electrodes 22, 23 of the quartz crystal resonator to an external measurement device to check the characteristic of the quartz crystal resonator 20. For example, by measuring the resonance frequency, the impedance, and so on while changing the voltage applied to the electrodes 22, 23 of the quartz crystal resonator 20 from the external measurement device, it is possible to determine whether the quartz crystal resonator 20 is a non-defective product or a defective product based on the magnitude or the variation of the measurement value.

As an example, the semiconductor device 30 has terminals 300 through 309. When the semiconductor device 30 is mounted on the first surface 11a of the first substrate 11, the terminals 300, 301 of the semiconductor device 30 are electrically connected to the pair of terminals 24 of the quartz crystal resonator 20 via the wiring patterns 50, 51, respectively. Further, the terminals 302 through 309 of the semiconductor device 30 are electrically connected respectively to the external connection terminals 62 through 69 via the wiring patterns 52 through 59, respectively.

The external connection terminals 62, 69 are used as power supply terminals respectively supplied with a power supply potential VCC and a reference potential VEE. The external connection terminals 63, 64 are used as output terminals for respectively outputting an inverted clock signal and a normal phase clock signal generated by the oscillation circuit. It should be noted that the clock signals are not required to be differential signals, and in that case, the number of terminals for outputting the clock signal can be one. The external connection terminals 65 through 67 are used as control terminals to be respectively supplied with digital control signals for updating the operation state of the oscillation circuit. It should be noted that it is sufficient for the number of control terminals to be supplied with the digital control signals to be equal to or greater than one. The external connection terminal 68 is supplied with an output enable signal.

The wiring patterns 50, 51 electrically connect the pair of terminals 24 of the quartz crystal resonator 20 and the oscillation circuit to each other, and are electrically connected respectively to the monitor terminals 60, 61 at the same time. It should be noted that it is also possible to cut a part of each of the wiring patterns 50, 51 with a laser, or remove the monitor terminals 60, 61 after the adjustment of the resonance frequency of the quartz crystal resonator 20 or the like is performed.

The wiring pattern 52 is electrically connected to the power supply terminal 62 to be supplied with the power supply potential VCC, and the wiring pattern 59 is electrically connected to the power supply terminal 69 to be supplied with the reference potential VEE. The wiring patterns 53, 54 are electrically connected respectively to the output terminals 63, 64 for outputting the clock signals generated by the oscillation circuit. The wiring patterns 55 through 57 are electrically connected respectively to the control terminals 65 through 67 to be supplied with digital control signals for updating the operation state of the oscillation circuit. The wiring pattern 58 is electrically connected to the external connection terminal 68 to be supplied with the output enable signal.

In the present embodiment, the output terminals 63, for outputting the clock signals generated by the oscillation circuit are arranged along a first side 10a of the package 10. On the other hand, the control terminals 65, 66 to be supplied with the digital control signals for updating the operation state of the oscillation circuit are arranged along a second side 10b of the package 10. Alternatively, the control terminal 67 to be supplied with the digital control signal for updating the operation state of the oscillation circuit is arranged along a second side 10d of the package 10. It should be noted that the "second side" denotes a side different from the first side 10a.

By disposing the output terminals 63, 64 for outputting the clock signals and the control terminals 65 through 67 to be supplied with the digital control signals respectively on the different sides of the package 10 in the quartz crystal oscillator 110 the oscillation frequency of which is dynamically digitally controlled during the oscillation operation as described above, it is possible to increase the distance between the wiring patterns 53, 54 for transmitting the clock signals and the wiring patterns 55 through 57 for transmitting the digital control signals to thereby reduce the capacitive coupling between the wiring patterns 53, 54 and the wiring patterns 55 through 57, and thus reduce the deterioration of the oscillation accuracy due to the interference by the digital control signals.

Further, the wiring patterns 50, 51 for electrically connecting the pair of terminals 24 of the quartz crystal resonator 20 and the oscillation circuit to each other are disposed so as to extend toward a third side 10c of the package. Thus, it is possible to make the wiring patterns 50, 51 sensitive to the noise distant from the transmission paths of the clock signals and the digital control signals to reduce the capacitive coupling between the wiring patterns 50, 51 and the transmission paths of the clock signals and the digital control signals, and thus reduce the deterioration of the oscillation accuracy due to the interference by the clock signals and the digital control signals.

Further, the wiring patterns 53, 54 electrically connected respectively to the output terminals 63, 64 do not cross the wiring patterns 50, 51 in a planar view, and the wiring patterns 55 through 57 electrically connected respectively to the control terminals 65 through 67 do not cross the wiring patterns 50 through 54 in a planar view. It should be noted that in the present specification, the "planar view" denotes an action of seeing through each part from a direction perpendicular to the principal surface of the package 10.

Thus, it is possible to reduce the coupling capacitance between the wiring patterns 50, 51 sensitive to the noise, the wiring patterns 53, 54 for transmitting the clock signals, and the wiring patterns 55 through 57 for transmitting the digital control signals to thereby reduce the deterioration of the oscillation accuracy due to the interference by the clock signals and the digital control signals.

Further, the wiring pattern 52 electrically connected to the power supply terminal 62 to be supplied with the power supply potential VCC is disposed between the wiring pattern 51 and the wiring patterns 53, 54, and the wiring pattern 59 electrically connected to the power supply terminal 69 to be supplied with the reference potential VEE is disposed between the wiring pattern 50 and the wiring pattern 57.

Thus, it is possible to further reduce the coupling capacitance between the wiring pattern 50 or 51 sensitive to the noise and the wiring pattern 53, 54, or 57 for transmitting the clock signals or the digital control signals to thereby further reduce the deterioration of the oscillation accuracy due to the interference by the clock signals or the digital control signals.

In the semiconductor device 30, terminals 303, 304 for outputting the clock signals are arranged along a side closest to the first side 10a of the package 10 in the semiconductor device 30. On the other hand, terminals 305, 306 to be supplied with the digital control signals are arranged along a side closest to the second side 10b of the package 10 in the semiconductor device 30. Alternatively, the terminal 307 to be supplied with the digital control signal is arranged along a side closest to the second side 10d of the package 10 in the semiconductor device 30.

Thus, it is possible to shorten the wiring patterns 53, 54 for connecting the terminals 303, 304 of the semiconductor device 30 and the output terminals 63, 64 respectively to each other, and shorten the wiring patterns 55 through 57 for connecting the terminals 305 through 307 of the semiconductor device 30 and the control terminals 65 through 67 respectively to each other to thereby reduce the capacitive coupling between the wiring patterns 53, 54 and the wiring patterns 55 through 57, and thus reduce the deterioration of the oscillation accuracy due to the interference by the digital control signals.

Second Embodiment

Figure 3:
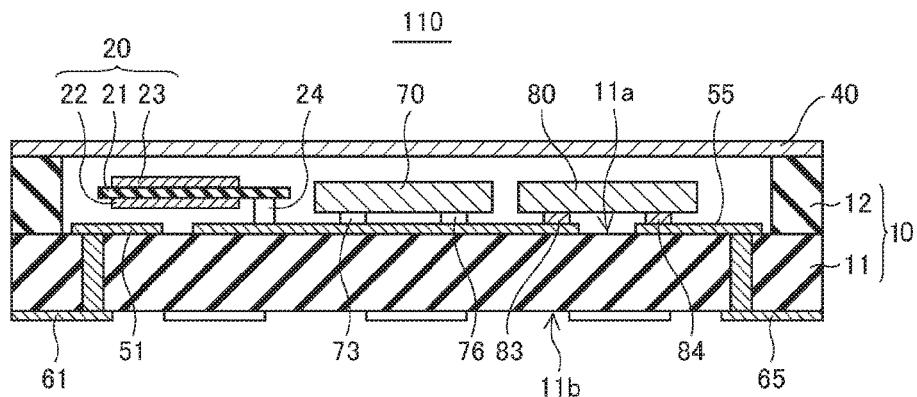
FIG. 3 is a cross-sectional view of a quartz crystal oscillator according to a second embodiment of the invention.

FIG. 3 is a cross-sectional view of a quartz crystal oscillator according to the second embodiment of the invention. In the second embodiment, instead of the semiconductor device 30 in the first embodiment shown in FIG. 1, a semiconductor device 70 for performing the oscillation operation to generate the clock signal and a semiconductor device 80 for controlling the oscillation frequency of the semiconductor device 70 due to the digital control signal constitute the oscillation circuit. Regarding other points, the second embodiment can be the same as the first embodiment.

The semiconductor devices 70, 80 are disposed on the first surface 11a of the first substrate 11 in the package 10. The semiconductor device 70 is electrically connected to the electrodes 22, 23 of the quartz crystal resonator 20 via the wiring layer disposed on the first surface 11a of the first substrate 11 and the pair of terminals 24 of the quartz crystal resonator 20. Each of the semiconductor devices 70, 80 can also be a semiconductor chip (a bare chip) not encapsulated in a package. The bare chip is mounted on the first surface 11a of the first substrate 11 using flip-chip bonding or the like.

Figure 4:
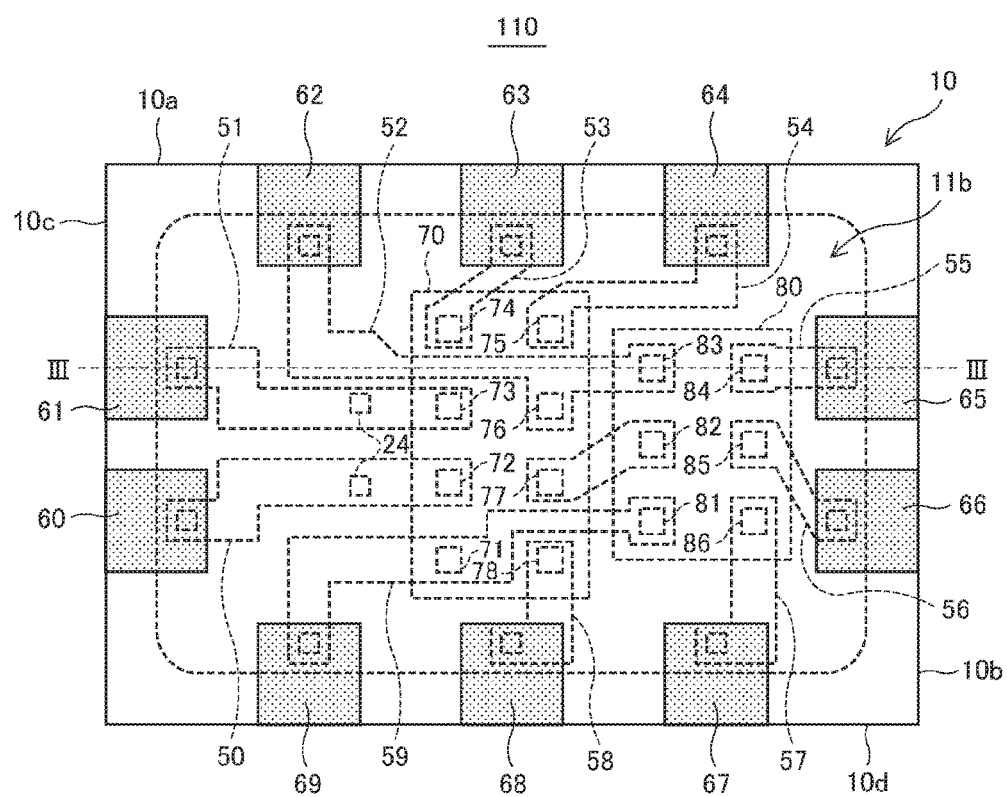
FIG. 4 is a bottom view of the quartz crystal oscillator shown in FIG. 3.

FIG. 4 is a bottom view of the quartz crystal oscillator shown in FIG. 3. The line III-III in FIG. 4 indicates the position of the cross-section shown in FIG. 3. As shown in FIG. 4, the package 10 has four sides 10a through 10d.

The quartz crystal oscillator 110 has a wiring layer including the plurality of wiring patterns 50 through 59 and so on disposed on the first surface 11a of the first substrate 11 in the package 10. A part of each of the wiring patterns constitutes an IC connection pad to be electrically connected to one of the terminals of the semiconductor device 70 or 80.

Further, The quartz crystal oscillator 110 has the plurality of external connection terminals 60 through 69 disposed on the second surface 11b of the first substrate 11 in the package 10. The first substrate 11 is provided with the plurality of through holes, and the wiring patterns 50 through 59 and the external connection terminals 60 through 69 are electrically connected respectively to each other via these through holes.

As an example, the semiconductor device 70 has terminals 71 through 78, and the semiconductor device 80 has terminals 81 through 86. When the semiconductor devices 70, 80 are mounted on the first surface 11a of the first substrate 11, the terminals 72, 73 of the semiconductor device 70 are electrically connected to the pair of terminals 24 of the quartz crystal resonator 20 via the wiring patterns 50, 51, respectively.

Further, the terminals 74, 75 are electrically connected to the output terminals 63, 64 via the wiring patterns 53, 54, respectively. The terminals 76, 71 are electrically connected to the output terminals 62, 69 via the wiring patterns 52, 59, respectively. The terminal 78 is electrically connected to the external connection terminal 68 via the wiring pattern 58.

The terminal 77 of the semiconductor device 70 is electrically connected to the terminal 82 of the semiconductor device 80 via a wiring pattern. Thus, the control voltage output from the terminal 82 of the semiconductor device 80 is supplied to the terminal 77 of the semiconductor device 70. The terminals 83, 81 of the semiconductor device 80 are electrically connected to the power supply terminals 62, 69 via the wiring patterns 52, 59, respectively. The terminals 84 through 86 are electrically connected to the control terminals 65 through 67 via the wiring patterns 55 through 57, respectively.

Also in the present embodiment, the output terminals 63, 64 for outputting the clock signals generated by the oscillation circuit are arranged along the first side 10a of the package 10. On the other hand, the control terminals 65, 66 to be supplied with the digital control signals for updating the operation state of the oscillation circuit are arranged along the second side 10b of the package 10. Alternatively, the control terminal 67 to be supplied with the digital control signal for updating the operation state of the oscillation circuit is arranged along the second side 10d of the package 10.

By disposing the output terminals 63, 64 for outputting the clock signals and the control terminals 65 through 67 to be supplied with the digital control signals respectively on the different sides of the package 10 in the quartz crystal oscillator 110 the oscillation frequency of which is dynamically digitally controlled during the oscillation operation as described above, it is possible to increase the distance between the wiring patterns 53, 54 for transmitting the clock signals and the wiring patterns 55 through 57 for transmitting the digital control signals to thereby reduce the capacitive coupling between the wiring patterns 53, 54 and the wiring patterns 55 through 57, and thus reduce the deterioration of the oscillation accuracy due to the interference by the digital control signals.

Further, the wiring patterns 50, 51 for electrically connecting the pair of terminals 24 of the quartz crystal resonator 20 and the oscillation circuit to each other are disposed so as to extend toward a third side 10c of the package. Thus, it is possible to make the wiring patterns 50, 51 sensitive to the noise distant from the transmission paths of the clock signals and the digital control signals to reduce the capacitive coupling between the wiring patterns 50, 51 and the transmission paths of the clock signals and the digital control signals, and thus reduce the deterioration of the oscillation accuracy due to the interference by the clock signals and the digital control signals.

Further, the wiring patterns 53, 54 electrically connected respectively to the output terminals 63, 64 do not cross the wiring patterns 50, 51 in a planar view, and the wiring patterns 55 through 57 electrically connected respectively to the control terminals 65 through 67 do not cross the wiring patterns 50 through 54 in a planar view.

Thus, it is possible to reduce the coupling capacitance between the wiring patterns 50, 51 sensitive to the noise, the wiring patterns 53, 54 for transmitting the clock signals, and the wiring patterns 55 through 57 for transmitting the digital control signals to thereby reduce the deterioration of the oscillation accuracy due to the interference by the clock signals and the digital control signals.

Further, the wiring pattern 52 electrically connected to the power supply terminal 62 to be supplied with the power supply potential VCC is disposed between the wiring pattern 51 and the wiring patterns 53, 54, and the wiring pattern 59 electrically connected to the power supply terminal 69 to be supplied with the reference potential VEE is disposed between the wiring pattern 50 and the wiring pattern 57.

Thus, it is possible to further reduce the coupling capacitance between the wiring pattern 50 or 51 sensitive to the noise and the wiring pattern 53, 54, or 57 for transmitting the clock signals or the digital control signals to thereby further reduce the deterioration of the oscillation accuracy due to the interference by the clock signals or the digital control signals.

In the semiconductor devices 70, 80, the terminals 74, 75 for outputting the clock signals are arranged along a side closest to the first side 10a of the package 10 in the semiconductor device 70. On the other hand, terminals 84, 85 to be supplied with the digital control signals are arranged along a side closest to the second side 10b of the package 10 in the semiconductor device 80. Alternatively, the terminal 86 to be supplied with the digital control signal is arranged along a side closest to the second side 10d of the package 10 in the semiconductor device 80.

Thus, it is possible to shorten the wiring patterns 53, 54 for connecting the terminals 74, 75 of the semiconductor device 70 and the output terminals 63, 64 respectively to each other, and shorten the wiring patterns 55 through 57 for connecting the terminals 84 through 86 of the semiconductor device 80 and the control terminals 65 through 67 respectively to each other to thereby reduce the capacitive coupling between the wiring patterns 53, 54 and the wiring patterns 55 through 57, and thus reduce the deterioration of the oscillation accuracy due to the interference by the digital control signals.

Configuration of PLL Circuit

Figure 5:
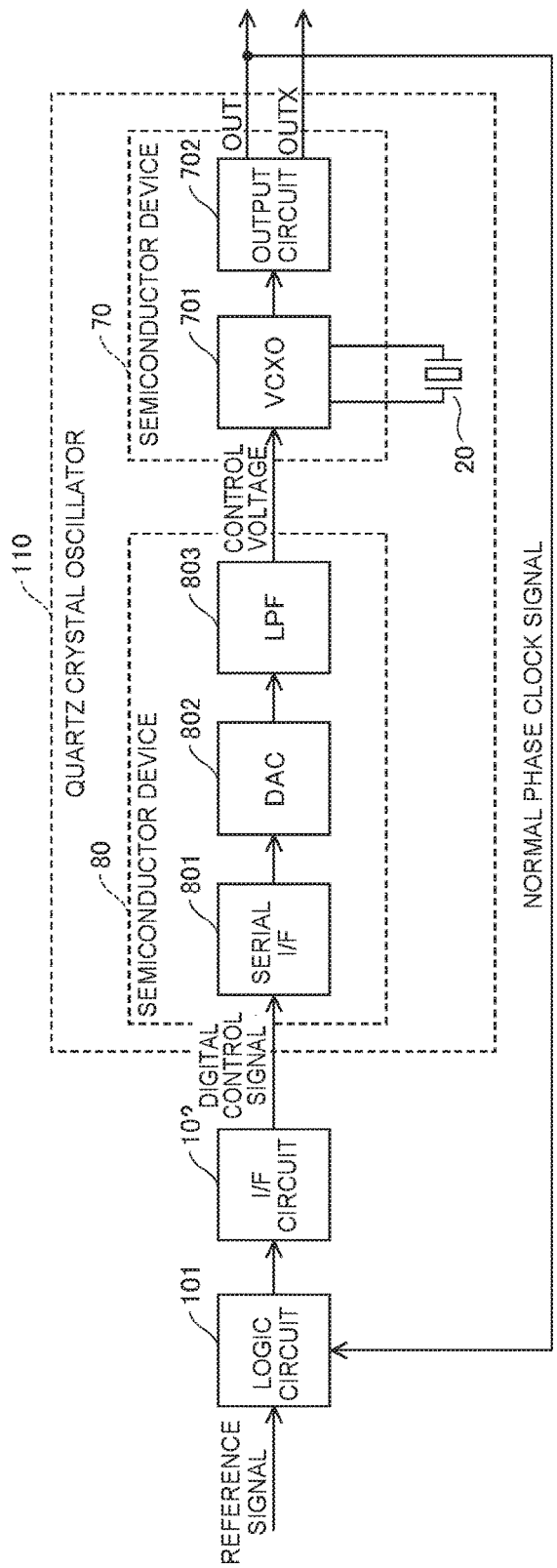
FIG. 5 is a block diagram showing a configuration example of a PLL circuit using the quartz crystal oscillator according to the embodiment.

FIG. 5 is a block diagram showing a configuration example of a PLL circuit using the quartz crystal oscillator according to one of the first and second embodiments of the invention. As shown in FIG. 5, the PLL circuit includes a logic circuit 101, an interface (I/F) circuit 102, and the quartz crystal oscillator 110. Hereinafter, the PLL circuit using the quartz crystal oscillator according to the second embodiment will be described as an example.

The quartz crystal oscillator 110 includes a serial interface (I/F) 801, a digital-to-analog converter (DAC) 802, a low-pass filter (LPF) 803, a voltage-controlled quartz crystal oscillator (VCXO) 701, and an output circuit 702. Here, the serial interface 801 through the LPF 803 are incorporated in the semiconductor device 80, and the VCXO 701 and the output circuit 702 are incorporated in the semiconductor device 70.

Figure 6:
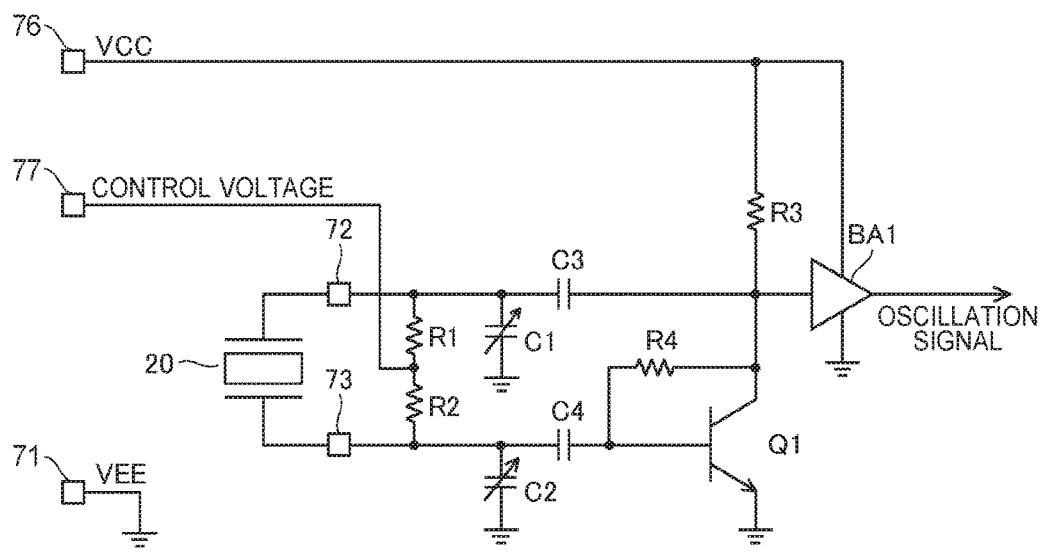
FIG. 6 is a circuit diagram showing a configuration example of a VCXO shown in FIG. 5.

FIG. 6 is a circuit diagram showing a configuration example of the VCXO shown in FIG. 5. As shown in FIG. 6, the VCXO 701 includes an NPN bipolar transistor Q1, capacitors C1 through C4, resistors R1 through R4, and a buffer amplifier BA1. Between the terminal 72 and the terminal 73, there is connected the quartz crystal resonator 20.

The terminal 76 is supplied with the power supply potential VCC, and the terminal 71 is supplied with the reference potential VEE. The resistors R1, R2 are connected in series between the two electrodes of the quartz crystal resonator 20. The capacitors C1, C2 are respectively connected between the two electrodes of the quartz crystal resonator 20 and an interconnection of the reference potential VEE. The capacitor C3 is connected between one of the electrodes of the quartz crystal resonator 20 and the collector of the transistor Q1. The capacitor C4 is connected between the other of the electrodes of the quartz crystal resonator 20 and the base of the transistor Q1.

The collector of the transistor Q1 is connected to an interconnection of the power supply potential VCC via the resistor R3, and the emitter is connected to the interconnection of the reference potential VEE. The resistor R4 is connected between the collector and the base of the transistor Q1. The buffer amplifier BA1 buffers the oscillation signal generated in the collector of the transistor Q1 to supply the output circuit 702 shown in FIG. 5. The output circuit 702 generates the normal phase clock signal OUT and the inverted clock signal OUTX based on the oscillation signal and then outputs these signals to an external circuit, for example. The normal phase clock signal OUT is also supplied to the logic circuit 101.

The transistor Q1 performs an inverting amplification operation, and the oscillation signal generated in the collector is fed back to the base via the quartz crystal resonator 20 and so on. On this occasion, the quartz crystal resonator 20 vibrates due to the alternating-current voltage applied by the transistor Q1. The vibration is significantly excited at the natural resonance frequency, and the quartz crystal resonator 20 acts as a negative resistance. As a result, the VCXO 701 oscillates at an oscillation frequency determined mainly by the resonance frequency of the quartz crystal resonator 20.

It should be noted that the oscillation frequency of the VCXO 701 can be fine-tuned by changing the capacitance value of the capacitor C1 or the capacitor C2. Therefore, in the example shown in FIG. 6, the capacitors C1, C2 are each constituted by a variable-capacitance diode (varactor diode) with the capacitance value varying in accordance with the control voltage supplied to the terminal 77, for example. The variable-capacitance diode changes the capacitance value in accordance with a reverse bias voltage applied between the cathode and the anode.

Referring again to FIG. 5, the logic circuit 101 compares the phase or the frequency of the normal clock signal OUT supplied from the output circuit 702 with the phase or the frequency of a reference signal to thereby generate an error signal, and then outputs the error signal to the interface circuit 102. The interface circuit 102 generates the digital control signals for updating the operation state of the VCXO 701 based on the error signal output by the logic circuit 101. In the serial transmission of the digital control signals, the SPI standard, the I²C standard, or the like can be used.

For example, it is possible for the interface circuit 102 to generate a serial clock signal for performing the serial transmission, serial control data for adjusting the oscillation frequency, and a chip-select signal for selecting the semiconductor device (chip). The interface circuit 102 outputs these digital control signals to the serial interface 801 incorporated in the semiconductor device 80. The serial clock signal and the control data to be noise sources are output respectively to the terminals 84, 86 shown in FIG. 4.

The serial interface 801 receives the digital control signals output from the interface circuit 102, and then supplies the DAC 802 with the control data. The DAC 802 converts the control data supplied by the serial interface 801 into a control voltage. The LPF 803 performs a low-pass filter process on the control voltage output from the DAC 802. The control voltage output from the LPF 803 is supplied to the VCXO 701 via the terminal 77 shown in FIG. 4. Thus, the oscillation frequency of the VCXO 701 can externally be controlled.

Figure 7:
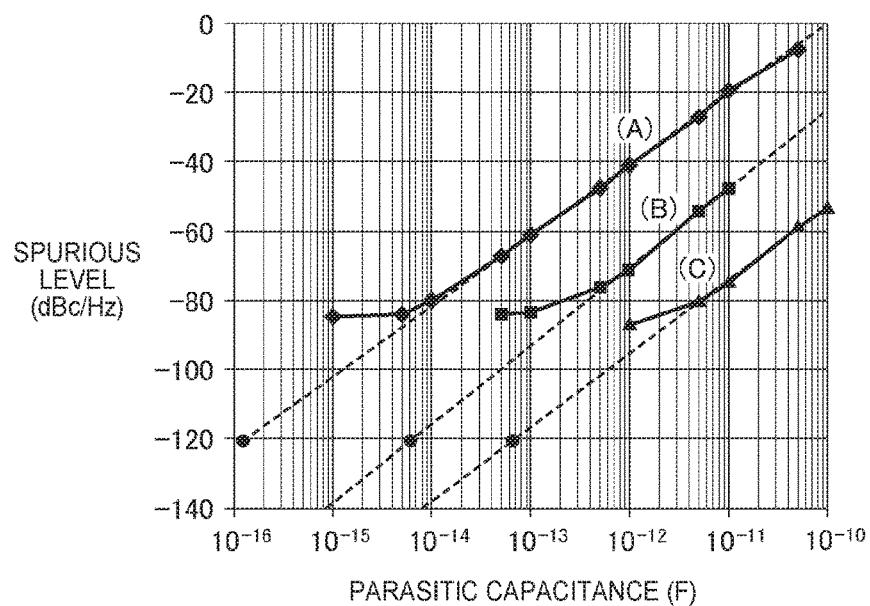
FIG. 7 is a diagram showing a relationship between the parasitic capacitance between a plurality of terminals, and the spurious level.

FIG. 7 is a diagram showing a relationship between the parasitic capacitance between a plurality of terminals and the spurious level in the oscillation signal. In FIG. 7, the horizontal axis represents the parasitic capacitance (F), and the vertical axis represents the spurious level (dBc/Hz) per 1 Hz with respect to the fundamental wave (carrier). The spurious denotes components other than the fundamental wave, which is generated by harmonic waves, subharmonic waves, parasitic vibrations, and so on. Further, the solid lines represent measurement values, and include measurement error. On the other hand, the dotted lines represent calculation values.

The (A) part in FIG. 7 shows the relationship between the parasitic capacitance between the terminal 73 of the semiconductor device 70 and the terminal 86 of the semiconductor device 80 shown in FIG. 4, and the spurious level. According to the calculation value, in order to obtain the spurious level of −120 dBc/Hz, it is necessary to set the parasitic capacitance between the terminals to $1.14 \times 10^{-16}$ F.

The (B) part in FIG. 7 shows the relationship between the parasitic capacitance between the terminal 72 of the semiconductor device 70 and the terminal 86 of the semiconductor device 80 shown in FIG. 4, and the spurious level. According to the calculation value, in order to obtain the spurious level of −120 dBc/Hz, it is necessary to set the parasitic capacitance between the terminals to $6.05 \times 10^{-15}$ F.

The (C) part in FIG. 7 shows the relationship between the parasitic capacitance between the terminal 77 of the semiconductor device 70 and the terminal 86 of the semiconductor device 80 shown in FIG. 4, and the spurious level. According to the calculation value, in order to obtain the spurious level of −120 dBc/Hz, it is necessary to set the parasitic capacitance between the terminals to $6.28 \times 10^{-14}$ F.

In general, the power Pb of the noise of the digital signal to be mixed in the fundamental wave is expressed as Formula (1) below defining the voltage of the digital signal as Vd, the parasitic capacitance (coupling capacitance) between the noise source and the noise receiver as Cd, and the capacitance between the noise receiver and the interconnection of the reference potential as Cg.

$$Pd=QV=Cd^3 \cdot Cg/(Cd+Cg)^3 \cdot Vd^2 \qquad (1)$$

Here, the voltage Vd of the digital signal is determined by the electronic apparatus used, and the capacitance Cg of the noise receiver affects the variable range of the oscillation frequency. Therefore, the voltage Vd of the digital signal and the capacitance Cg of the noise receiver cannot be changed. Therefore, the influence of the noise is not reduced unless the parasitic capacitance Cd is reduced.

Meanwhile, the power Pa of the analog noise input to a control voltage input terminal of the VCXO is expressed as Formula (2) below defining the voltage of the analog noise as Va.

$$Pa=(Cd+Cg) \cdot Va^2 \qquad (2)$$

In the oscillator performing the digital control, it is desired that the digital noise is made sufficiently smaller than the analog noise to thereby obtain the noise characteristic equivalent to that of the oscillator performing the analog control. Therefore, the value of the parasitic capacitance Cd for fulfilling the condition of Pd<Pa is calculated with Formula (1) and Formula (2) as follows.

For example, substituting a typical insertion capacitance of 10 pF for Cg, the same voltage as the power supply voltage of 3.3 V for Vd, and a typical noise level of 60 $nV/Hz^{1/2}$ for Va, the parasitic capacitance Cd for fulfilling the condition of Pd<Pa is calculated from Formula (1) and Formula (2) as 0.069 aF (atto-Farad; $10^{-18}$ F) or smaller. The value corresponds to about one 150-thousandth of the capacitance Cg of the noise receiver.

The parasitic capacitance Cd is expressed as Formula (3) below.

$$Cd=\varepsilon 0 \cdot \varepsilon r \cdot S/r \qquad (3)$$

Here, $\varepsilon 0$ denotes the electric constant, $\varepsilon r$ denotes the specific permittivity of an insulating material, S denotes the area of the opposing part between the noise source pattern and the noise receiver pattern extending side by side, and r denotes the distance between the noise source pattern and the noise receiver pattern.

In order to reduce the parasitic capacitance Cd, it is sufficient to decrease the opposing area S between the two patterns or increase the distance r between the two patterns. Therefore, each of the embodiments of the invention focuses on increasing the distance r between the noise source pattern and the noise receiver pattern to thereby decrease the capacitive coupling between the noise source pattern and the noise receiver pattern, and thus reduce the deterioration of the oscillation accuracy due to the interference by the digital control signals and so on.

Electronic Apparatus

Then, an electronic apparatus using the quartz crystal oscillator according to any of the embodiments of the invention will be described.

Figure 8:
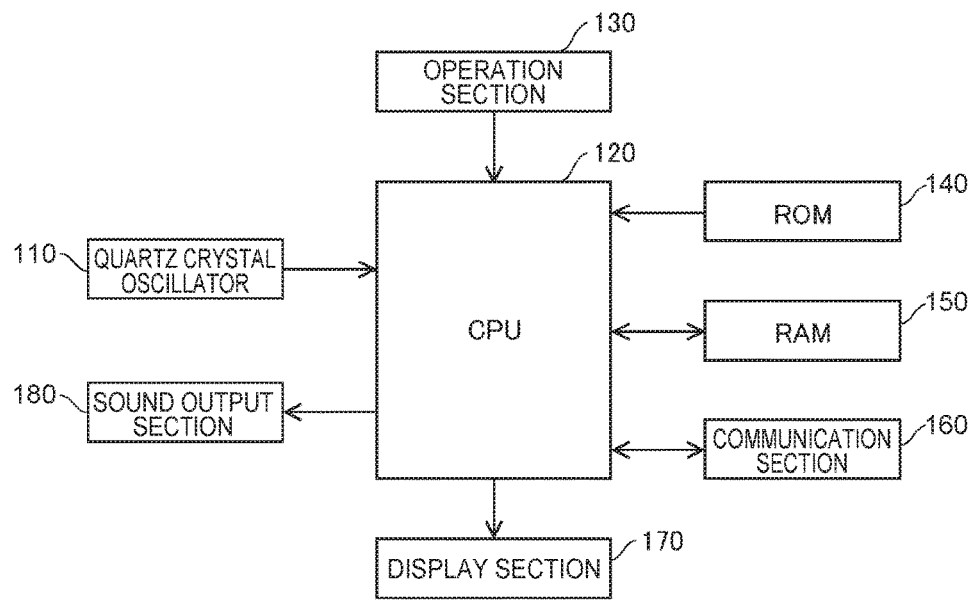
FIG. 8 is a block diagram showing a first configuration example of an electronic apparatus according to an embodiment of the invention.

FIG. 8 is a block diagram showing a first configuration example of the electronic apparatus according to an embodiment of the invention. The electronic apparatus includes the quartz crystal oscillator 110 according to any one of the embodiments of the invention, a CPU 120, an operation section 130, a read-only memory (ROM) 140, a random-access memory (RAM) 150, a communication section 160, a display section 170, and a sound output section 180. It should be noted that it is also possible to eliminate or modify some of the constituents shown in FIG. 8 or to add other constituents to the constituents shown in FIG. 8.

The quartz crystal oscillator 110 performs the oscillation operation at the oscillation frequency controlled by the digital control signals to thereby generate the clock signal. The clock signal generated by the quartz crystal oscillator 110 is supplied to each section of the electronic apparatus via the CPU 120 or the like.

The CPU 120 operates in sync with the clock signal supplied from the quartz crystal oscillator 110, and performs a variety of signal processing and control processing in accordance with programs stored in the ROM 140 and so on. For example, the CPU 120 performs a variety of signal processing in accordance with the operation signal supplied from the operation section 130, and controls the communication section 160 for performing data communication with the outside. Alternatively, the CPU 120 generates an image signal for making the display section 170 display a variety of images, and generates a sound signal for making the sound output section 180 output a variety of sounds.

The operation section 130 is an input device including, for example, operation keys, button switches, and outputs the operation signal corresponding to the operation by the user to the CPU 120. The ROM 140 stores the programs, data, and so on for the CPU 120 to perform the variety of types of signal processing and control processing. Further, the RAM 150 is used as a working area of the CPU 120, and temporarily stores the program and data retrieved from the ROM 140, the data input using the operation section 130, the calculation result obtained by the CPU 120 performing operations in accordance with the programs, or the like.

The communication section 160 is constituted by, for example, an analog circuit and a digital circuit, and performs the data communication between the CPU 120 and the external devices. The display section 170 includes, for example, a liquid crystal display device (LCD), and displays a variety of information based on the image signal supplied by the CPU 120. Further the sound output section 180 includes, for example, a speaker, and outputs a sound based on the sound signal supplied by the CPU 120.

As the electronic apparatus described above, there can be cited, for example, a mobile terminal such as a cellular phone, a digital still camera, a digital movie, a television set, a video phone, a security video monitor, a head-mounted display, a personal computer, a printer, network equipment, a compound machine, on-vehicle equipment (e.g., navigation system), an electric calculator, an electronic dictionary, a computerized game machine, a robot, measurement equipment, and medical equipment (e.g., an electronic thermometer, an electronic manometer, an electronic blood sugar meter, an electrocardiogram measurement instrument, an ultrasonograph, and an electronic endoscope).

Figure 9:
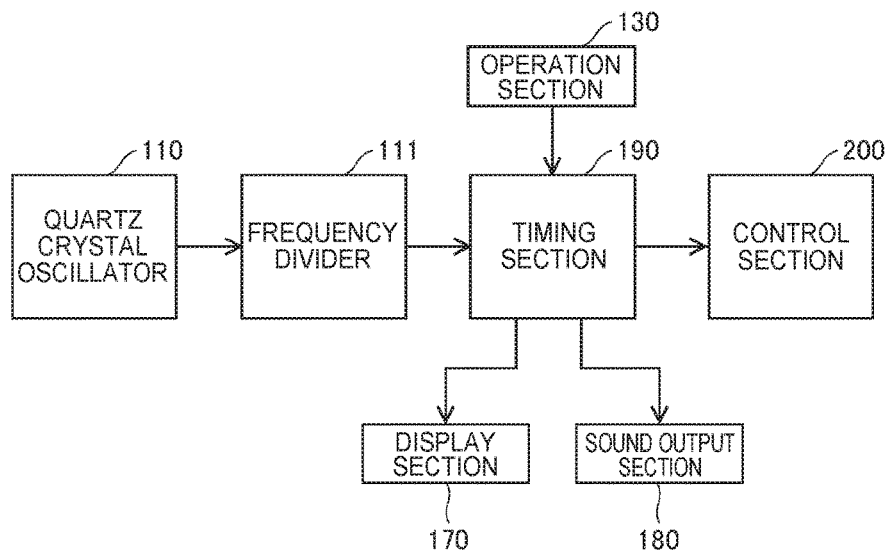
FIG. 9 is a block diagram showing a second configuration example of an electronic apparatus according to an embodiment of the invention.

FIG. 9 is a block diagram showing a second configuration example of the electronic apparatus according to an embodiment of the invention. In this example, a timepiece and a timer will be described. The timepiece according to an embodiment of the invention includes the quartz crystal oscillator 110 according to any one of the embodiments of the invention, a frequency divider 111, the operation section 130, the display section 170, the sound output section 180, and the timing section 190. Further, the timer according to an embodiment of the invention includes a control section 200 instead of the sound output section 180. It should be noted that it is also possible to eliminate or modify some of the constituents shown in FIG. 9 or to add other constituents to the constituents shown in FIG. 9.

The frequency divider 111 is constituted by, for example, a plurality of flip-flops, and divides the frequency of the clock signal supplied from the quartz crystal oscillator 110 to generate a divided clock signal for timing. The timing section 190 is constituted by, for example, a counter, and performs a timing operation based on the divided clock signal supplied from the frequency divider 111 to generate a display signal representing the current time and an alarm time, and an alarm signal for generating an alarm sound.

The operation section 130 is used for setting the current time and the alarm time to the timing section 190. The display section 170 displays the current time and the alarm time in accordance with the display signal supplied from the timing section 190. The sound output section 180 generates the alarm sound in accordance with the alarm signal supplied from the timing section 190.

In the case of the timer, a timer function is provided instead of the alarm function. Specifically, the timing section 190 generates a timer signal representing the fact that the current time has coincided with the preset time. The control section 200 turns ON or OFF the equipment connected to the timer in accordance with the timer signal supplied from the timing section 190.

According to the present embodiment, it is possible to provide an electronic apparatus operating with the accurate clock signals generated using the quartz crystal oscillator 110 in which the deterioration of the oscillation accuracy due to the interference by the digital control signals and so on is reduced.

Moving Object

Then, a moving object using the quartz crystal oscillator according to any of the embodiments of the invention will be described. As the moving object, there can be cited, for example, a vehicle, a self-propelled robot, a self-propelled carrying apparatus, a train, a boat and ship, an airplane, and an artificial satellite.

Figure 10:
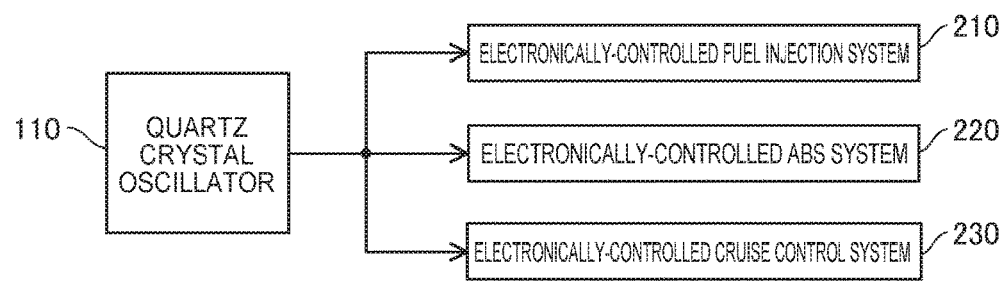
FIG. 10 is a block diagram showing a configuration example of a moving object according to an embodiment of the invention.

FIG. 10 is a block diagram showing a configuration example of a moving object according to an embodiment of the invention. As shown in FIG. 10, the moving object includes the quartz crystal oscillator 110 according to any one of the embodiments of the invention, and is further equipped with electronically-controlled devices such as an electronically-controlled fuel injection system 210, an electronically-controlled ABS system 220, and an electronically-controlled cruise control system 230. It should be noted that it is also possible to eliminate or modify some of the constituents shown in FIG. 10 or to add other constituents to the constituents shown in FIG. 10.

The quartz crystal oscillator 110 performs the oscillation operation at the oscillation frequency controlled by the digital control signals to thereby generate the clock signal. The clock signal generated by the quartz crystal oscillator 110 is supplied to the electronically-controlled fuel injection system 210, the electronically-controlled ABS system 220, the electronically-controlled cruise control system 230, or the like.

The electronically-controlled fuel injection system 210 operates in sync with the clock signal supplied from the quartz crystal oscillator 110, and sprays the liquid fuel into the intake air in a misty state at a predetermined timing in a premixed combustion engine such as a gasoline engine. The electronically-controlled ABS (antilock braking system) system 220 operates in sync with the clock signal supplied from the quartz crystal oscillator 110, and repeats the operation of driving the brake with the gradually increasing strength, and releasing the brake once when the moving object starts slipping, and then driving the brake again, when the operation is performed so as to put on the brake. The electronically-controlled cruise control system 230 operates in sync with the clock signal supplied from the quartz crystal oscillator 110, and controls the accelerator and the brake so as to keep the speed of the moving object constant while monitoring the speed of the moving object.

According to the present embodiment, it is possible to provide a moving object operating with the accurate clock signals generated using the quartz crystal oscillator 110 in which the deterioration of the oscillation accuracy due to the interference by the digital control signals and so on is reduced.

Although in the embodiments described above, the quartz crystal oscillator using the quartz crystal resonator is described, the invention is not limited to the embodiments described hereinabove, but can also be applied to oscillators using piezoelectric materials other than quartz crystal. As described above, it is possible for those skilled in the art to make a number of modifications within the scope or the spirit of the invention.

The entire disclosure of Japanese Patent Application No. 2015-220119, filed Nov. 10, 2015 is expressly incorporated by reference herein.

What is claimed is:

1. An oscillator comprising:
a package having a first side, a second side, a third side, and a fourth side;
a resonator and an oscillation circuit disposed in the package;
an output terminal disposed outside the package and arranged along the first side of the package, and outputting a clock signal generated by the oscillation circuit;
a control terminal disposed outside the package and arranged along the second side of the package, and supplied with a digital control signal adapted to update an operation state of the oscillation circuit;
a first wiring pattern and a second wiring pattern disposed in the package, electrically connecting a pair of terminals of the resonator and the oscillation circuit to each other, and extending toward the third side of the package;
a third wiring pattern disposed in the package, electrically connected to the output terminal, and having no crossing with the first and second wiring patterns in a planar view;
a fourth wiring pattern disposed in the package, electrically connected to the control terminal, and having no crossing with the first through third wiring patterns in the planar view; and
a fifth wiring pattern disposed between one of the first and second wiring patterns and one of the third and fourth wiring patterns in the package, and electrically connected to a power supply terminal supplied with one of a power supply potential and a reference potential.

2. The oscillator according to claim 1, wherein
at least one semiconductor device constituting the oscillation circuit has a first terminal arranged along a side, which is closest to the first side of the package, of the semiconductor device, and adapted to output the clock signal, and a second terminal arranged along a side, which is closest to the second side of the package, of the semiconductor device, and supplied with the digital control signal.

3. An oscillator comprising:

a package;

a resonator and an oscillation circuit disposed in the package;

a first wiring pattern and a second wiring pattern disposed in the package, and adapted to electrically connect a pair of terminals of the resonator and the oscillation circuit to each other;

a third wiring pattern disposed in the package, electrically connected to an output terminal adapted to output a clock signal generated by the oscillation circuit, and having no crossing with the first and second wiring patterns in a planar view;

a fourth wiring pattern disposed in the package, electrically connected to a control terminal supplied with a digital control signal adapted to update an operation state of the oscillation circuit, and having no crossing with the first through third wiring patterns in the planar view; and a fifth wiring pattern disposed between one of the first and second wiring patterns and one of the third and fourth wiring patterns in the package, and electrically connected to a power supply terminal supplied with one of a power supply potential and a reference potential.

4. An electronic apparatus comprising:

the oscillator according to claim 1.

5. An electronic apparatus comprising:

the oscillator according to claim 3.

6. A moving object comprising:

the oscillator according to claim 1.

7. A moving object comprising:

the oscillator according to claim 3.

* * * * *